United States Patent [19]

Riede et al.

[11] 4,293,409

[45] Oct. 6, 1981

[54] ARTIFICIAL KIDNEY DIALYSATE PREPARATION SYSTEM

[75] Inventors: Gerhard Riede, Vellinge; Lars-Åke L. Larsson, Löddenköpinge; Roland J. E. Andersson, Bjärred; Sven A. Jösson, Staffanstorp; Lars J. C. Travén, Lund, all of Sweden

[73] Assignee: Gambro AB, Sweden

[21] Appl. No.: 964,275

[22] Filed: Nov. 28, 1978

Related U.S. Application Data

[63] Continuation of Ser. No. 841,899, Oct. 13, 1977, abandoned.

[30] Foreign Application Priority Data

Oct. 14, 1976 [SE] Sweden .............................. 7611389

[51] Int. Cl.³ .............................................. B01D 31/00
[52] U.S. Cl. : .................................. 210/96.2; 210/188; 210/321.3
[58] Field of Search ................. 210/22, 321 B, 180, 210/186, 96 M, 188

[56] References Cited

U.S. PATENT DOCUMENTS

| | | | |
|---|---|---|---|
| 3,441,136 | 4/1969 | Serfass et al. | 210/321 B |
| 3,515,275 | 6/1970 | Bowman | 210/22 |
| 3,598,727 | 8/1971 | Willock | 210/321 B X |
| 3,809,241 | 5/1974 | Alvine | 210/186 X |
| 3,827,561 | 8/1974 | Serfass et al. | 210/180 |
| 4,060,485 | 11/1977 | Eaton | 210/96 M X |
| 4,137,160 | 1/1979 | Ebling et al. | 210/22 A |

FOREIGN PATENT DOCUMENTS 1417570 12/1975 United Kingdom ............. 210/22 A

Primary Examiner—Frank A. Spear, Jr.
Attorney, Agent, or Firm—Lerner, David, Littenberg & Samuel

[57] ABSTRACT

A dialysis system is disclosed for treatment of a first fluid with dialysis fluid, the dialysis fluid being a mixture of water and dialysis concentrate. The system comprises a dialyzer, a source of water, a source of dialysis concentrate, first and second fluid conducting means communicating with the sources of water and dialysis concentrate, pump means associated with the first and second fluid conducting means, and third fluid conducting means for conducting fluid from the pump means to the dialyzer. The pump means serves to draw water and dialysis concentrate through the first and second fluid conducting means respectively, and to mix the water and dialysis concentrate so that a mixture of water and dialysis concentrate is conducted through the third fluid conducting means.

9 Claims, 1 Drawing Figure

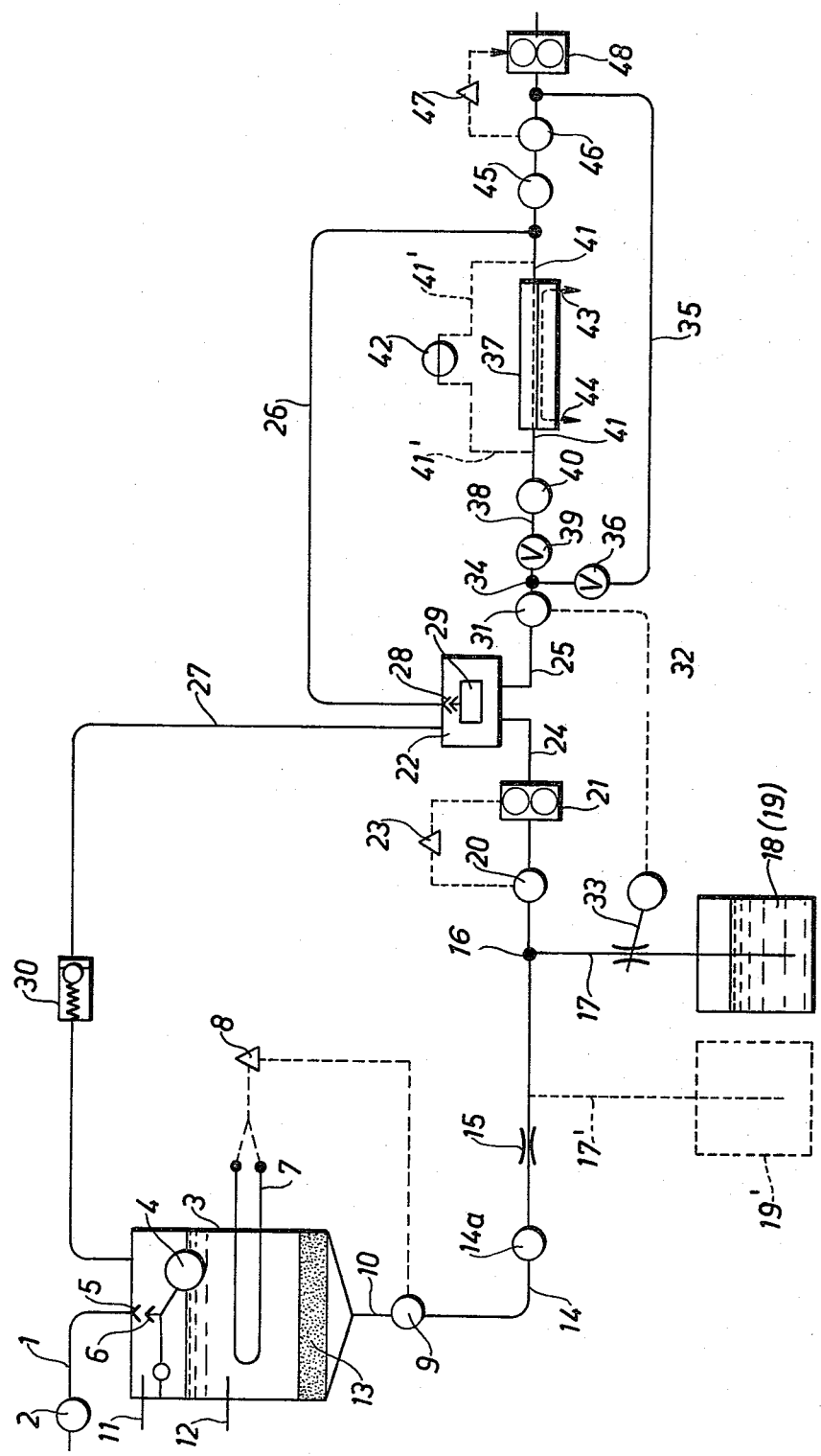

ARTIFICIAL KIDNEY DIALYSATE PREPARATION SYSTEM

This is a continuation of application Ser. No. 841,899, filed Oct. 13, 1977, now abandoned.

BACKGROUND OF THE INVENTION

The present invention relates generally to dialysis systems, and more particularly to a dialysis system having a source of water and a source of dialysis concentrate which are to be mixed to provide dialysis fluid for the dialyzer.

It is the object of the invention, among other things, to provide a simplification of earlier used dialysis systems of the above-mentioned type. Moreover, it aims at achieving the greatest possible effectiveness and safety.

SUMMARY OF THE INVENTION

The dialysis system of the present invention includes a dialyzer, a source of water and a source of dialysis concentrate, first and second fluid conducting means communicating with the sources of water and dialysis concentrate, pump means associated with the first and second fluid conducting means, and third fluid conducting means for conducting fluid from the pump means to the dialyzer. The pump means serves to draw water and dialysis concentrate through the first and second fluid conducting means respectively, and to mix the water and dialysis concentrate so that a mixture of water and dialysis concentrate is conducted through the third fluid conducting means.

In a preferred embodiment of the present invention, gas removal means are provided in the third fluid conducting means for the purpose of removing gas bubbles in the mixture of water and dialysis concentrate. In a further preferred embodiment, throttling means are interposed in the first fluid conducting means so that the throttling means, the pump means and the gas removal means cooperate with one another to remove gas bubbles in the water being drawn through the first and third conducting means.

These and further features and characteristics of the present invention will be described in more detail hereinbelow with reference to the enclosed drawing which by way of example describes the preferred embodiment of the dialysis system according to the present invention.

BRIEF DESCRIPTION OF THE DRAWING

The single FIGURE is a schematic diagram of the dialysis system according to the present invention.

DETAILED DESCRIPTION OF THE PRESENT INVENTION

Referring to the FIGURE, an inlet line 1 for fresh water leads to a water tank 3 and is provided with an inlet valve 2 for controlling the introduction of water into the tank 3. The water tank 3 is provided with a float valve 4 which is adapted to close the water intake 5 with the help of a shut-off cone 6 when the water tank 3 is full. The water tank 3, moreover, comprises means 7 for heating the water, e.g. in the form of a heating coil. This heating coil is controlled in a well known manner by a temperature controller 8 which in turn is responsive to the temperature measured by a temperature transmitter 9 in the outlet line 10 from the tank 3. Furthermore, the tank comprises high and low level controllers shown schematically and marked 11 and 12 respectively for monitoring the liquid level in the tank 3. These level controllers may be adapted for example to control directly the inlet valve 2. Finally, the tank 3 comprises a filter element 13 shown schematically which in the first hand is intended to remove solid particles from the water, but which in practice also removes a certain amount of gas in the water, e.g. free gas-bubbles.

After heating, the fresh water delivered to tank 3 is conducted via the outlet line 10, temperature transmitter 9, a line 14 with a shut-off valve 14a and a throttle valve 15 to a branching-off point 16. Here, a branch line 17 is connected which under normal circumstances, i.e. when a first fluid, e.g. blood, is being treated with dialysis fluid, starts from a source 18 of dialysis concentrate, e.g. a salt solution concentrate. Usually, when the dialysis fluid comprises a salt solution, this source quite simply consists of a keg of concentrated salt solution.

In the sterilization of the system, in accordance with the invention more fully described in copending U.S. application Ser. No. 841,898 filed simultaneously herewith now U.S. Pat. No. 4,158,034, Oct. 13, 1977 this keg 18 of concentrated salt solution is replaced with a keg or container having sterilizing agent which thus constitutes the source of sterilizing agent and which is designated (19) in the FIGURE. This is the simplest solution in practice since the same supply line 17 is used for both the dialysis concentrate and the sterilizing agent. However, if required for special reasons, it is of course also possible to connect a further line 17' to the system parallel with line 17 for the connection of a separate vessel 19'. This has been indicated in the FIGURE by broken lines. As a sterilizing agent, conventional substances on the market may be used, such as for example, formalin or chloramine.

From the point 16 the liquid flows via a pressure pick-up 20 and a pump 21 to a bubble separator 22. The pressure pick-up 20 controls the pump 21 in a well known manner via a pressure controller 23. The feed line to the bubble separator 22 is designated 24. From the bubble separator 22 there leads firstly an ordinary fluid conducting line 25, secondly a line 26 for the removal of separated gas, and thirdly a fluid return line 27. The inlet 28 to the line 26 is controlled by a float valve 29, which closes this inlet 28 when the bubble separator 22 is filled with liquid, in connection with sterilization. The return line 27 is provided with a spring-loaded check valve 30 and leads back to the liquid tank 3. The function of return line 27 and check valve 30 in connection with sterilization of the dialysis system is more fully described in the aforementioned U.S. Pat. No. 4,158,034.

The ordinary fluid conducting line 25 leads to a conductively meter 31. With the help of a controller 32 which is responsive to the conductivity of the fluid measured by meter 31, the meter 31 effectively controls the opening and closing of a variable throttle valve 33 in the line 17. In this way, an effective and accurate drawing of dialysis concentrate from source 18 can be achieved to provide the desired proportions of dialysis concentrate and water which go to form the dialysis fluid for the dialyzer.

After the conductivity meter 31 the liquid flow reaches a new branching-off point 34 from which departs a shunt line 35 with a valve 36. The shunt line 35 is used in the event a by-passing of the dialyzer 37 by the liquid flow is required quickly, e.g. if a fault is discovered in the dialysis liquid in respect of, for example, the temperature or the salt content. Otherwise, the liquid flows normally to the dialyzer 37 via the line 38 which contains a valve 39 and a flow meter 40. The valve 39 is normally controlled together with the valve 36 for the changeover of the liquid flow. Alternatively, the two valves 36 and 39 can of course be replaced by a three-way valve located at the branching-off point 34.

Numeral 41 designates the lines or tubes which are normally connected to the dialyzer 37. In the event of sterilization, however, these tubes are connected to a "safety by-pass" 42, which is indicated by broken lines marked 41'. An embodiment of such a "safety by-pass" is described, by way of example, in U.S. application Ser. No. 771,257, filed Feb. 23, 1977 now U.S. Pat. No. 4,122,010. It need therefore not be described in detail in conjunction with the present invention. The inlet and outlet of the dialyzer 37 for the fluid, e.g. blood, to be treated with dialysis fluid, are designated 43 and 44 respectively. The dialyzer 37 may take almost any conventional form of dialyzer, such as for example, that described in U.S. Pat. Nos. 3,411,630 and 3,516,548.

Numeral 45 designates a blood detector which gives an alarm and possibly shuts down the whole system if blood is detected in the dialysis fluid exiting from the dialyzer 37. This blood detector 45 may for example, be a transparent tube placed opposite an otherwise screened photocell device which directly monitors the occurance of any blood in the dialysis fluid. After the blood detector 45, the liquid flow passes a pressure gauge 46 which via a controller 47 controls a liquid pump 48. Finally, the liquid flow is passed to a drain, provided no part of the flow is to be recirculated. Such recirculation is well known, however, to those versed in the art and has therefore not been shown in detail in the drawing.

Thus, in accordance with the present invention, a single pump 21 serves both to draw water and dialysis concentrate from their respective sources 3 and 18, and to mix such drawn water and dialysis concentrate to form the dialysis fluid for the dialyzer 37. As described above, the desired and/or proper proportioning of water and dialysis concentrate is achieved by means of the conductivity meter 31, controller 32 and variable throttle valve 33. Also, it is preferred that the pressure pickup 20, which controls the pump 21 via controller 23, be placed downstream of the branch line 17 which is connected to the source of dialysis concentrate.

The pump 21 further serves to deaerate the water (and thus the mixed dialysis fluid) by virtue of being combined on one side with a throttling device 15 located between the pump 21 and the water tank 3 and on the other side with a bubble separator 22 placed downstream of the pump 21.

Furthermore, it is to be noted that, by virtue of the second suction pump 48 being disposed downstream of the dialyzer 37, the two pumps, 21 and 48, can be controlled so that a vacuum as well as overpressure can be generated on the dialysis liquid side of the dialyzer 37. In connection with this, the second pump is appropriately controlled by controller 47 which is responsive to the pressure measured by pressure gauge 46, suitably placed between the dialyzer 37 and pump 48.

Sterilization of the dialysis system is fully described in the aforementioned copending U.S. Pat. No. 4,158,034 and therefore need not be further described herein.

Naturally, the invention is not limited solely to the example described above, but may be modified within the scope of the following claims. Thus, the components forming part of the system may be varied in respect of shape as well as function without exceeding the scope of the invention. Moreover, details which are not necessary for the understanding of the invention but which to those versed in the art are self-evident parts of a complete dialysis system have not been shown in the drawing.

What is claimed is:

1. A dialysis system for treating a first fluid with dialysis fluid, the dialysis fluid being a mixture of water and dialysis concentrate, said system comprising:
   a dialyzer;
   a source of water;
   a source of dialysis concentrate;
   first fluid conducting means communicating with said source of water;
   second fluid conducting means communicating with said source of dialysis concentrate;
   a single pump in fluid communication with said first and second fluid conducting means for drawing water from said source of water through said first fluid conducting means, for drawing dialysis concentrate from said source of dialysis concentrate through said second fluid conducting means, and for mixing water and said dialysis concentrate prior to its introduction into said dialyzer;
   third fluid conducting means for conducting said mixture of water and dialysis concentrate from said single pump to and through said dialyzer;
   gas removal means in said third fluid conducting means for removing gas bubbles from said mixture of water and dialysis concentrate; and
   throttling means interposed in said first conducting means;
   said throttling means, said single pump and said gas removal means cooperating with one another to deaerate said mixture of water and dialysis concentrate.

2. The dialysis system of claim 1 further including fourth fluid conducting means communicating with each of said first and second fluid conducting means and with said single pump for conducting said water and dialysis concentrate to said single pump, pressure measuring means for measuring the pressure in said fourth fluid conducting means, and pressure control means responsive to the pressure measured by said pressure measuring means for controlling said single pump.

3. The dialysis system of claim 2 further including proportioning means for controlling the portions of water and dialysis concentrate drawn through said first and second fluid conducting means.

4. The dialysis system of claim 3 wherein said proportioning means comprises detection means associated with said third fluid conducting means for detecting the proportions of dialysis concentrate in said third fluid conducting means, and concentration control means associated with said second fluid conducting means for controlling the amount of dialysis concentrate drawn through said second fluid conducting means, said concentration control means being responsive to the proportion of dialysis concentrate detected by said detection means in said third fluid conducting means.

5. The dialysis system of claim 4 wherein said concentration control means comprises a variable throttle valve interposed in said second fluid conducting means and a controller for controlling the variation in opening of said variable throttle valve in response to the proportion of dialysis concentrate detected by said detection means.

6. The dialysis system of claim 5 wherein said detection means comprises a conductivity meter for measuring the conductivity of the mixture of water and dialysis concentrate in said third fluid conducting means.

7. The dialysis system of claim 1 further including a second pump interposed in said third fluid conducting means at a position downstream of said dialyzer for drawing the mixture of water and dialysis concentrate through said dialyzer.

8. The dialysis system of claim 7 further including fourth fluid conducting means communicating with each of said first and second fluid conducting means and with said single pump for conducting said water and dialysis concentrate to said single pump; first pressure measuring means for measuring the pressure in said fourth fluid conducting means; first control means for controlling said single pump, said first control means being responsive to the pressure measuring means for measuring the pressure in said third fluid conducting means downstream of said dialyzer; and second control means for controlling said second pump, said second control means being responsive to the pressure measured by said second pressure measuring means.

9. A dialysis system for treating a first fluid with dialysis fluid, the dialysis fluid being a mixture of water and dialysis concentrate, said system comprising:
   a dialyzer;
   a source of water;
   a source of dialysis concentrate;
   first fluid conducting means communicating with said source of water;
   second fluid conducting means communicating with said source of dialysis concentrate;
   a single pump in fluid communication with said first and second fluid conducting means for drawing water from said source of water through said first fluid conducting means, for drawing dialysis concentrate from said source of dialysis concentrate through said second fluid conducting means, and for mixing said water and said dialysis concentrate prior to its introduction into said dialyzer;
   at least one fluid restricting means in one of said first and second fluid conducting means for controlling the amount of water and dialysis concentrate withdrawn by said single pump to provide a desired proportion of water and dialysis concentrate to be mixed to form said dialysis fluid;
   third fluid conducting means for conducting said mixture of water and dialysis concentrate from said single pump to and through said dialyzer;
   gas removal means in said third fluid conducting means for removing gas bubbles from said mixture of water and dialysis concentrate; and
   throttling means interposed in said first fluid conducting means, said throttling means, said single pump and said gas removal mean cooperating with one another to deaerate said mixture of water and dialysis concentrate.

* * * * *